(12) United States Patent
Drevin et al.

(10) Patent No.: US 9,101,677 B2
(45) Date of Patent: *Aug. 11, 2015

(54) STERILIZATION METHOD

(75) Inventors: Ingrid Drevin, Uppsala (SE); Hamid Houshmand, Uppsala (SE); Ola Lind, Uppsala (SE)

(73) Assignee: GE Healthcare Bio-Science AB, Uppsala (SE)

( * ) Notice: Subject to any disclaimer, the term of this patent is extended or adjusted under 35 U.S.C. 154(b) by 152 days.

This patent is subject to a terminal disclaimer.

(21) Appl. No.: 12/674,169

(22) PCT Filed: Aug. 27, 2008

(86) PCT No.: PCT/US2008/074383
§ 371 (c)(1),
(2), (4) Date: Feb. 19, 2010

(87) PCT Pub. No.: WO2009/032662
PCT Pub. Date: Mar. 12, 2009

(65) Prior Publication Data
US 2011/0178271 A1    Jul. 21, 2011

(30) Foreign Application Priority Data
Aug. 30, 2007 (GB) .................................. 0716900.6

(51) Int. Cl.
*A61L 2/07* (2006.01)
*B01D 15/20* (2006.01)
*B01J 20/286* (2006.01)
*B01J 20/32* (2006.01)
*B01J 20/34* (2006.01)

(52) U.S. Cl.
CPC . *A61L 2/07* (2013.01); *B01D 15/20* (2013.01); *B01J 20/286* (2013.01); *B01J 20/3274* (2013.01); *B01J 20/3466* (2013.01)

(58) Field of Classification Search
CPC ....... A61L 2/07; B01D 15/20; B01J 20/3466; B01J 20/3274; B01J 20/286
USPC .............. 210/635, 656, 659, 764, 198.2, 282; 96/101, 105
See application file for complete search history.

(56) References Cited

U.S. PATENT DOCUMENTS 3,706,631 A    12/1972   Falk
4,028,242 A *  6/1977   Kokurin et al. ............... 210/774
(Continued)

FOREIGN PATENT DOCUMENTS

EP       1 672 068       6/2006
WO       WO 87/04369     7/1987
(Continued)

OTHER PUBLICATIONS

Instructions 11-0026-01 AC.*
(Continued)

*Primary Examiner* — Ernest G Therkorn
(74) *Attorney, Agent, or Firm* — Parks Wood LLC

(57) ABSTRACT

The present invention relates to a method for sterilization of different materials, especially sensitive material, such as chromatographic media with sensitive ligands. The method for sterilization of a chromatographic separation medium comprises exposing the separation medium to pressurized steam at a temperature of between about 121° C. and about 135° C.

8 Claims, 2 Drawing Sheets

(56) References Cited

U.S. PATENT DOCUMENTS

| | | | |
|---|---|---|---|
| 4,923,068 A * | 5/1990 | Crowson | 210/741 |
| 5,268,144 A * | 12/1993 | Heilmann et al. | 422/26 |
| 5,423,982 A * | 6/1995 | Jungbauer et al. | 210/198.2 |
| 5,817,528 A | 10/1998 | Bohm et al. | |
| 7,682,510 B2 * | 3/2010 | Berglof et al. | 210/635 |
| 2005/0143566 A1 * | 6/2005 | Hober | 530/388.4 |
| 2006/0194955 A1 * | 8/2006 | Hober et al. | 530/388.1 |
| 2008/0142439 A1 * | 6/2008 | Berglof et al. | 210/636 |

FOREIGN PATENT DOCUMENTS

| | | | |
|---|---|---|---|
| WO | WO 03/080655 | | 10/2003 |
| WO | WO 2006/033634 | | 3/2006 |
| WO | WO 2006/096116 | | 9/2006 |
| WO | WO/2006/096116 | * | 9/2006 |

OTHER PUBLICATIONS

"Instructions 11-0026-01 AC—Affinity Chromatography—MabSelect SuRe" [Online] Sep. 2008, GE Healthcare Bio-Sciences, Retrieved from the Internet: URL:http://www4.gelifesciences.com/APTRIX/upp00919.nsf/content/248924095E7BDE84C1257628001D1958?OpenDocument&hometitle=tech_support_service. p. 1-p. 24.

* cited by examiner

STERILIZATION METHOD

CROSS-REFERENCE TO RELATED APPLICATIONS

This application is a filing under 35 U.S.C. §371 and claims priority to international patent application number PCT/US2008/074383 filed Aug. 27, 2008, published on Mar. 12, 2009, as WO 2009/032662, which claims priority to application number 0716900.6 filed in Great Britain on Aug. 30, 2007; the disclosure of which is incorporated herein by reference in its entirety.

FIELD OF THE INVENTION

The present invention relates to a method for sterilization of different materials, especially sensitive materials, and in particular chromatography media having affinity ligands bound thereto, such as proteinaceous ligands.

BACKGROUND OF THE INVENTION

The manufacture of biopharmaceuticals, particularly drugs based on bioactive molecules such as proteins, peptides and nucleic acids, requires the production and purification of these molecules on an industrial scale. In particular, the increasing demand for monoclonal antibodies (MAbs) as biopharmaceutical products has promoted the development of cell cultures with high expression levels and, as a consequence, the demand for more efficient purification processes has increased. For example, monoclonal antibodies are revolutionising the treatment of many illnesses and they have become one of the main indicators of the direction drug treatments are moving. The latest estimates of the European monoclonal antibody therapeutics market arrive at a figure of $11.4 billion (€ 8.7 billion) by 2011. This increased demand has necessitated the use of large, advanced chromatography systems comprising columns packed with separations media such as SEPHAROSE™, MABSELECT™, SOURCE™ and CAPTO™ (GE Healthcare).

During chromatographic separation of biopharmaceuticals, it is of critical importance to ensure that the process is conducted under sterile conditions and that potentially harmful contaminants are removed from the system before use. Contamination with bacteria and other microbes is an often encountered problem within many biotechnological and biomedical applications. Various agents are known for their ability to inactivate and/or destroy microbial populations, for example, sodium hydroxide, peracetic acid, phosphoric acid, ethylene oxide, chlorine dioxide and benzyl alcohol. However, disinfection of columns and chromatographic media is cumbersome, particularly disinfection of proteinaceous media, i.e. chromatographic media provided with proteinaceous ligands, such as various affinity chromatography media. The most effective disinfectants and sanitation reagents such as strong acids or alkalis, quaternary ammonium compounds, halogen-containing compounds, oxidizing agents, and phenols and related compounds are considered harmful to most chromatography media particularly to proteinaceous affinity media. In addition, sterilization methods, such as gamma irradiation and autoclaving, are also considered to have large deleterious effects on those media.

Furthermore, many sanitation or sterilization methods involving acids or alkalis, quaternary ammonium compounds, halogen-containing compounds, oxidizing agents, and phenols and related compounds are harmful and/or toxic. Thus, methods are required for the efficient sterilization of sensitive material, such as chromatographic media.

U.S. Pat. No. 5,817,528 (Böhm, W. et al) describes a method for producing a sterile and pyrogen-free column containing a matrix material to which a protein is coupled. Suitably, the protein coupled to the column is *Staphylococcus aureus* Protein A, or *Streptococcus* Protein G, or the protein may be an antibody such as anti-human LDL immunoglobulin or anti-human Ig immunoglobulin. The method provides a column matrix material such as an agarose which is chemically activated, using CNBr/triethylamine or using 1,1'-carbonyldiimidazole. The chromatography matrix material is preferably sterilized by steam sterilization at 115° C., before combining with pathogen-free, purified protein under aseptic conditions so as to couple the protein to the matrix material.

SUMMARY OF THE INVENTION

The present invention provides a new sterilization method for bacterial and/or viral contamination, particularly in chromatographic separation media used in the purification of biopharmaceutical materials. The inventors have found that chromatographic separation media having particular proteinaceous ligands as defined herein and being bound to a solid support matrix is surprisingly resistant to denaturation by sterilization by autoclaving.

Thus, in a first aspect, there is provided a method for sterilization of a chromatographic separation medium wherein the chromatographic separation medium comprises proteinaceous ligands bound to a solid support matrix, the method comprising exposing the chromatographic separation medium to pressurized steam at a temperature of between about 121° C. (250° F.) and about 135° C. (270° F.).

Suitable proteinaceous ligands are selected from the group consisting of antibody-binding molecules, particularly functional analogues of Protein A and Protein G. In one embodiment, the chromatographic separation medium comprises a solid support matrix having proteinaceous ligands bound thereto and wherein the proteinaceous ligand is an alkali-stabilised Protein A derived ligand.

In one embodiment, the chromatographic separation medium is exposed to pressurized steam under a pressure in the range from 2 bars to 35 bars.

In one embodiment, the chromatographic separation medium is exposed to pressurized steam under a pressure in the range from 30-35 bars, more preferably under a pressure in the range from 34-35 bars.

In one embodiment, the chromatographic separation medium is exposed to pressurized steam for a time period in the range from 10 to 60 minutes.

In a particular embodiment, the chromatographic separation medium comprising a solid support matrix having proteinaceous ligands bound thereto is sterilized by exposure of the medium to pressurized steam at a temperature of 121° C. and 34 bars for 12 minutes.

Preferably, the chromatographic separation medium to be sterilized is contained in a chromatography column or supported on a filter.

DETAILED DESCRIPTION OF THE INVENTION

Figure 1:
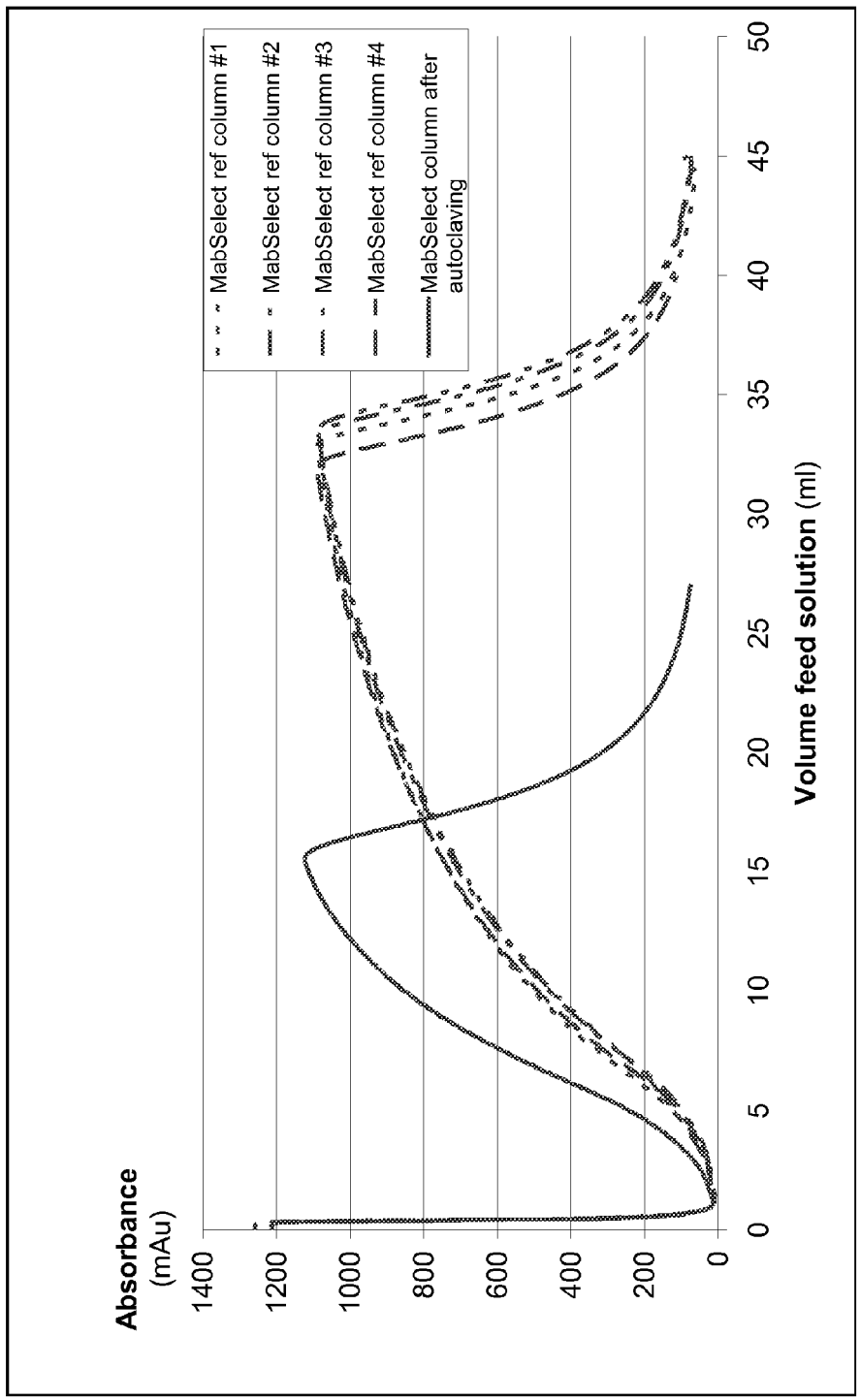
FIG. 1 is a plot showing the dynamic IgG binding capacity of a reference sample of MABSELECT™, compared with MABSELECT™ after autoclaving at 121° C., 34.4 bars for 12 minutes.
Figure 2:
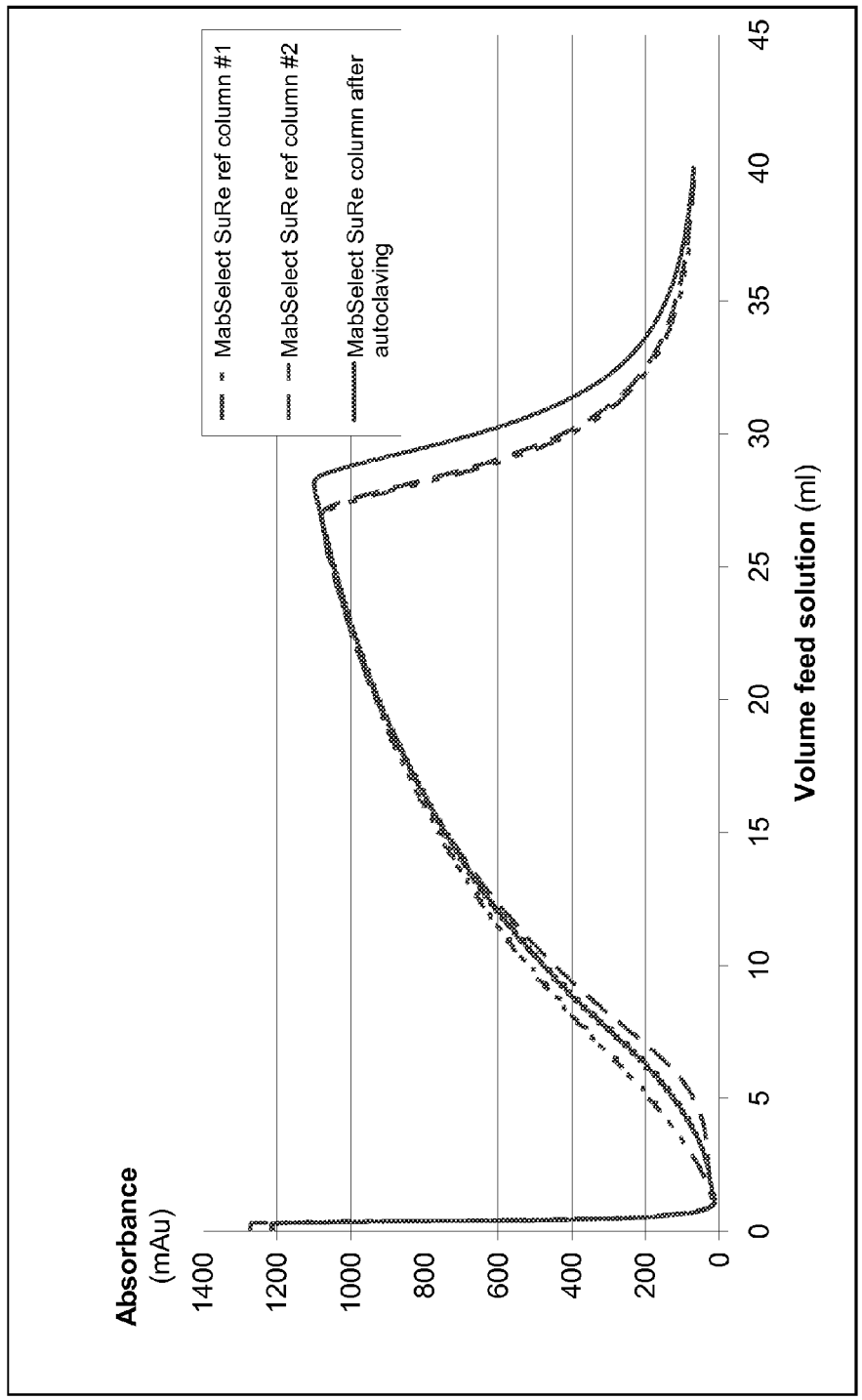
FIG. 2 is a plot showing the dynamic binding capacity of a reference sample of MABSELECT SURE™, compared with MABSELECT SURE™ after autoclaving at 121° C., 34.4 bars for 12 minutes.

The present invention provides a new and efficient method for sterilization of chromatography columns/media and filters, particularly a chromatographic separation medium having proteinaceous ligands bound thereto. In particular, the invention relates to a method for bacterial and viral inactivation of chromatographic separation media having an alkaline stabilised protein-A derived ligand attached thereto. The method is based on an exposure of separation media to pressurized steam at a temperature of between about 121° C. and about 135° C., more particularly between about 121° C. and about 123° C. In a particularly preferred embodiment, the chromatographic separation medium is exposed to pressurized steam at a temperature of 121° C.

Generally, moist heat sterilization by autoclaving refers to heating a material in an autoclave (e.g. gravity displacement apparatus) under a pressure of at least 2 bars to achieve a temperature of between about 121° C. and about 135° C. In the sterilization process, microorganisms are killed by heating in the presence of moisture and elevated pressure. See for example, "Understanding the Operation & Validation of Autoclaves: A Practical Approach", Reeks, B., BDR Publishing (September 1999). The sterilization period required is dependent on both the temperature and the size of the sample to be sterilized and can be in the range from 10 to 60 minutes. As the temperature and pressure are increased, the time required to achieve complete sterilization can normally be reduced, as shown in Table 1.

TABLE 1

| Temperature (° C.) | Time (minutes) | Pressure (bars, abs) |
| --- | --- | --- |
| 121-124 | 15 | 2.01 |
| 126-129 | 10 | 2.4 |
| 134-137 | 3 | 3.05 |

Conventionally, chromatography media, in the form of packed columns, cannot be sterilized by autoclaving because the column packing may be destroyed. Thus, chromatography media is usually sanitized (reduction of the numbers of microbial contaminants to an acceptable level), rather than by the complete sterilization of the media. To test the method for sterilizing chromatographic separation medium described herein, the inventors have utilized the elevated temperatures and pressures obtainable with the ASE® 200 Accelerated Solvent Extraction System (Dionex Corp) so as to keep water below its boiling point. The ASE® 200 instrument can be programmed for temperature, time and pressure. Since the lower pressure limit obtainable with the ASE® 200 instrument is ~34 bars, the inventors were able to evaluate high pressure steam sterilization performed at normal sterilization temperatures required, i.e. 121° C.

As used herein, the term "chromatographic separation medium" refers to a stationary or particulate phase which is effective to bind (i.e. adsorb) an analyte under selected mobile phase conditions, and to release the analyte under other selected mobile phase conditions. The process described herein is particularly suitable for sterilizing chromatographic media containing proteinaceous ligands bound thereto. A preferred chromatographic separation medium is MABSELECT SURE™. MABSELECT SURE™ (Superior Resistance) is a chromatography medium disclosed in WO 03/080655 (Hober, S) and is based on an alkali-stabilised protein A-derived ligand, in which the amino acid sequence of the protein has been mutated by substitution of at least one asparagine residue with an amino acid other than glutamine, as compared with the parent protein ligand. When employed in a chromatographic separation medium, the mutated protein ligand exhibits an increased binding capacity during two or more separations with intermittent alkaline cleaning, as compared with a separation medium comprising the parent protein molecule. Preferably, the proteinaceous ligand as described herein is an Fc-fragment-binding protein that can be used for selective binding of IgG, IgA and/or IgM proteins, more preferably IgG.

The solid support matrix of the separation medium according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, optionally in N-substituted forms), amino (—NH$_2$, optionally in substituted form), oligo- or polyethyleneoxy groups on their external and, if present, also on internal surfaces. In one embodiment, the polymers may, for instance, be based on polysaccharides, such as dextran, starch, cellulose, pullulan, agarose etc., which advantageously have been cross-linked, for instance with bis-epoxides, epihalohydrins, 1,2,3-trihalo-substituted lower hydrocarbons, to provide a suitable porosity and rigidity. In the most preferred embodiment, the solid support is porous agarose beads.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid.

In yet another alternative, the solid support may be of inorganic nature, e.g. silica, zirconium oxide, etc.

In a further yet another embodiment, the solid support is in another form such as a surface, a chip, capillaries, or a filter.

The ligand may be attached to the support via conventional coupling techniques utilising, e.g. amino and/or carboxy groups present in the ligand. Bis-epoxides, epichlorohydrin, CNBr, N-hydroxysuccinimide ester (NHS) etc are well-known coupling reagents. A spacer group can be introduced between the support and the ligand, thereby improving the availability of the ligand and facilitating the chemical coupling of the ligand to the support. Alternatively, the ligand may be attached to the support by non-covalent bonding, such as physical adsorption or biospecific adsorption.

The method is particularly suitable for the sterilization of media susceptible to degradation under harsh conditions, such as MABSELECT SURE™.

The sterilization method is widely applicable and may be used for sterilizing chromatography media intended for any purpose, such as the isolation of bioactive molecules including antibodies (particularly monoclonal antibodies), nucleic acids (for example, genomic DNA, RNA), and for the isolation and separation of cells from biological samples.

The sterilization method is suitable also for disposable columns and filters. The disposable columns/filters give the advantage of being ready-to-use without any need of further cleaning and sterilization. This implies columns/filters with good sterility or at least free of microbial contamination.

As used herein, the term biological sample refers to a sample obtained from any biological source, including samples of biological tissue or cells obtained harvested in vivo or in situ, that contains or is suspected of containing nucleic acids or polypeptides such as monoclonal antibodies.

The invention also provides a chromatographic separation medium sterilized by a method as disclosed in any of appended claims 1 to 6, in particular the medium, MABSELECT SURE™.

The invention is further illustrated by reference to the following example and figures in which:

EXAMPLE

Below the present invention will be disclosed by way of examples, which are intended solely for illustrative purposes and should not be construed as limiting the present invention as defined in the appended claims. All references mentioned below or elsewhere in the present application are hereby included by reference.

1. Moist Heat (Steam) sterilization

MABSELECT™ and MABSELECT SURE™ media were subjected to moist heat sterilization (autoclaving) under a pressure of 34.4 bars and a temperature of 121° C. for 12 minutes. For this purpose, 33 ml gel was packed in a column of an Accelerated Solvent Extractor (ASE® 200) from Dionex, USA with a 0.1M NaCl solution and exposed to 121° C. and 34.4 bars for 12 minutes. ASE® 200 is a high pressure instrument offering programmable pressure and heat with a minimum pressure at 34.4 bars.

The IgG binding capacity of exposed gels of MABSELECT™ and MABSELECT SURE™ media were measured in comparison with the untreated gels. The dynamic binding capacity data for untreated (reference columns 1-4) and autoclave-treated media are shown in Tables 2 and 3. $DBC_{n\%}$ is the dynamic binding capacity measured at n % breakthrough.

The results demonstrate that moist heat sterilization according to the method described herein had no effect on MABSELECT SURE™ binding capacity. On the other hand, MABSELECT™ lost 45% of its IgG binding capacity following moist heat sterilization under the same conditions.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A method for sterilization of a chromatographic separation medium wherein the chromatographic separation medium comprises proteinaceous ligands bound to a solid support matrix, the method comprising exposing the chromatographic separation medium to pressurized steam at a temperature of between about 121° C. and about 135° C.; wherein the amino acid sequence of said proteinaceous ligands has been mutated by substitution of at least one asparagine residue with an amino acid other than glutamine as compared with the parent protein ligand, wherein the chromatographic separation medium to be sterilized is an alkali-stabilised protein A-derived ligand bound to a support matrix.

2. The method of claim 1, wherein said chromatographic separation medium is exposed to pressurized steam under a pressure in the range from 2 bars to 35 bars.

3. The method of claim 1, wherein said chromatographic separation medium is exposed to pressurized steam under a pressure in the range from 30-35 bars.

4. The method of claim 1, wherein said chromatographic separation medium is exposed to pressurized steam under a pressure in the range from 34-35 bars.

TABLE 2

| MABSELECT SURE ™ | | | | |
|---|---|---|---|---|
| Reference Column 1 (mg/ml media) | Reference Column 2 (mg/ml media) | Reference Column 3 (mg/ml media) | Reference Column 4 (mg/ml media) | Autoclaved Media (mg/ml media) |
| $DBC_{5\%}$ 7.2 | 5.7 | 7.8 | 7.6 | 3.0 |
| $DBC_{10\%}$ 11.1 | 10.6 | 12.3 | 11.9 | 6.3 |
| $DBC_{50\%}$ 47.2 | 30.9 | 31.4 | 30.6 | 17.2 |

TABLE 3

| MABSELECT SURE ™ | | |
|---|---|---|
| Reference Column 1 (mg/ml media) | Reference Column 2 (mg/ml media) | Autoclaved Media (mg/ml media) |
| $DBC_{5\%}$ 9.7 | 2.2 | 4.7 |
| $DBC_{10\%}$ 13.9 | 6.5 | 9.3 |
| $DBC_{50\%}$ 30.1 | 27.3 | 30.4 |

5. The method of claim 1, wherein said chromatographic separation medium is exposed to pressurized steam for a time period in the range from 10 to 60 minutes.

6. The method of claim 1, wherein said chromatography medium is exposed to steam under a pressure of 34.4 bars and at a temperature of about 121° C.

7. The method of claim 1, wherein said chromatographic separation medium to be sterilized is contained in a chromatography column or supported on a filter.

8. The method of claim 1, wherein said proteinaceous ligands are Fc-fragment-binding proteins.

* * * * *